United States Patent [19]
Patton

[11] 3,964,972
[45] *June 22, 1976

[54] MODIFIED HETEROPOLYSACCHARIDES

[76] Inventor: John Tinsman Patton, 1213 E. Houghton Ave., Houghton, Mich. 49931

[ * ] Notice: The portion of the term of this patent subsequent to Apr. 24, 1990, has been disclaimed.

[22] Filed: July 24, 1972

[21] Appl. No.: 274,658

Related U.S. Application Data

[62] Division of Ser. No. 15,590, March 2, 1970, Pat. No. 3,729,460.

[52] U.S. Cl. ............................................... 195/31 P
[51] Int. Cl.² ....................................... C12D 13/04
[58] Field of Search ................ 195/31 P; 260/209 R

[56] References Cited

UNITED STATES PATENTS

| | | | |
|---|---|---|---|
| 3,096,293 | 7/1963 | Jeanes et al. | 195/31 P |
| 3,382,229 | 5/1968 | Patton et al. | 260/209 R |
| 3,516,983 | 6/1970 | Colegrove | 260/209 R |

*Primary Examiner*—A. Louis Monacell
*Assistant Examiner*—Thomas G. Wiseman

[57] ABSTRACT

An improved thickening agent is prepared by reacting a heteropolysaccharide produced by bacteria of the genus Xanthomonas with an alkaline compound in an aqueous reaction media at elevated temperatures.

8 Claims, 1 Drawing Figure

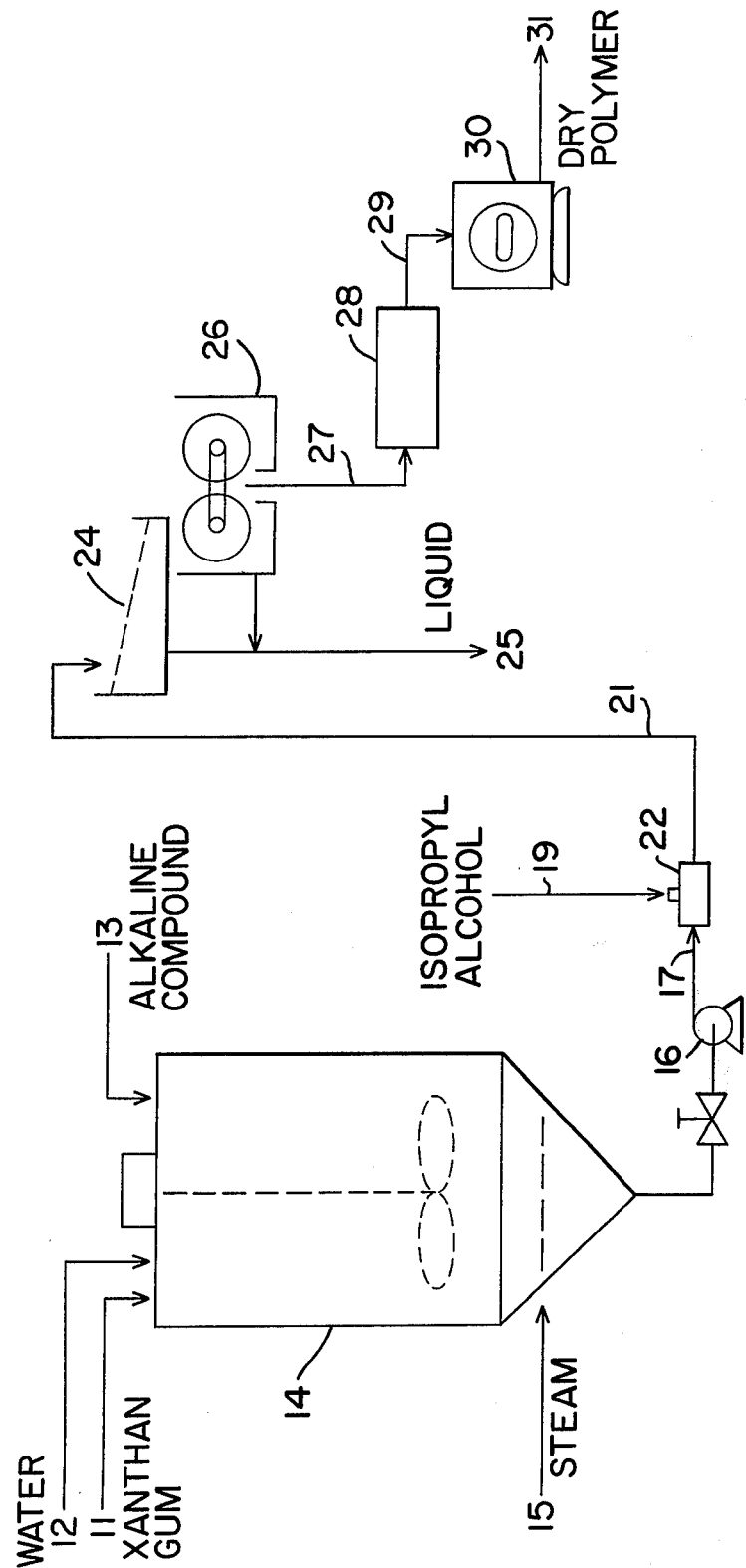

MODIFIED HETEROPOLYSACCHARIDES

This application is a division of application No. 15,590 filed Mar. 2, 1970, now U.S. Pat. No. 3,729,460.

The present invention relates to polymers for altering the rheological properties of aqueous media and more particularly related to a new class of modified heteropolysaccharides which are particularly effective for increasing the viscosities of brine and similar solutions. In still greater particularity, the invention relates to modified heteropolysaccharides produced by reacting an alkaline compound with xanthan gums, which are polymers derived by the action of bacteria of the genus Xanthomonas on carbohydrates.

The use of xanthan gums as thickening or bodying agents in foodstuffs, cosmetics, paints and pharmaceutical vehicles is well known. They are also effective as emulsifying, stabilizing and sizing agents. However, the inability of the gum to completely dissolve or disperse and thus produce clear, viscous solutions has held back wide spread application.

Interest in the development of more effective materials for thickening aqueous media has been spurred in recent years by indications that the use of such materials may permit significant improvements in secondary recovery operations carried out in the petroleum industry. Laboratory work and field tests have shown that the injection of a viscous solution in place of the water or brine normally employed in oil field waterflooding projects results in a substantial increase in the amount of crude oil which can be displaced from a subsurface reservoir during the course of such a project. The principal reason for this is that water, because its viscosity is lower than that of oil in place, tends to flow selectively through the more permeable sections of the reservoir during waterflooding. Much of the oil contained in the less permeable zones is bypassed by the water and is never recovered. The use of water or brine containing a thickening agent in concentrations sufficient to give viscosities more nearly equivalent to that of the oil reduces this tendency toward selective flow, and thus promotes more uniform piston-like displacement of the oil. The use of thickened water or brine in this manner promises to reduce significantly the amount of oil which must be left behind in the exploitation of petroleum reservoirs.

The chief obstacle to the wide spread use of viscous solutions during waterflooding operations carried out to date has been the lack of a satisfactory thickening agent. A number of polymers, gums and resins have been proposed as thickeners in the past. None of these has been found suitable. Most synthetic polymers, natural gums and resins, such as gum tragacanth, gum arabic, agar, alginic acid, gum ghatti and the like have only limited thickening powers and would have to be employed in concentrations that would make the cost of using them prohibitive. Even if their use were economically feasible, however, tests have shown that such materials are unsatisfactory. Solutions of many of them tend to lose their viscosity after exposure to elevated temperatures for only a short time. Others are rapidly degraded by brines and similar solutions. Still others, notably xanthan gum, tend to plug the porous surface of petroleum reservoirs. These and other considerations almost completely rule out such materials for use in waterflooding operations and other processes where an inexpensive, highly stable thickener is required.

SUMMARY OF THE INVENTION

Accordingly, it is the object of this invention to provide a simple, economic method of chemically modifying xanthan gum to obtain a purified product possessing the many desirable features now associated with xanthan gum, and in addition, high clarity, which is desired and often required when polymers are used to thicken certain foodstuffs, inks, dyes and especially solutions used in waterflooding petroleum reservoirs.

In accordance with the invention, it has now been found that heteropolysaccharides prepared by the fermentation of carbohydrates with bacteria of the genus Xanthomonas and subsequent reaction of the fermentation product with a base such as sodium hydroxide produce marked increases in the viscosities with little or no decrease in the clarity of brine and similar solutions to which they are added in low concentrations. Such heteropolysaccharides are stable for long periods at elevated temperatures and are not substantially degraded by salts normally found in oil field brines. They are not absorbed to a significant extent upon subsurface formations. These and other properties of the substituted heteropolysaccharides of the invention render them eminently suitable for thickening brines to be used in oil field secondary recovery processes and in a variety of other applications that require a highly stable thickener which is effective at low concentrations.

The reactions responsible for transforming this native xanthan gum to a polymer which, when dispersed in water, produces a clear, viscous liquid which has the appearance of a true solution, are complex and not fully defined. Deacetylation surely occurs almost immediately and yet clarity develops slowly, often requiring a reaction time of 2 to 3 hours. It is probable that hydrolysis and some degree depolymerization are the dominant mechanisms. When the reaction has proceeded to the desired extent, the modified polymer may be harvested by precipitation initiated by the addition of various alcohols, imines, amines, quaternary ammonium salts or polyvalent cations, followed by drying. Alternatively, the clarified reaction mixture can be dried directly to yield a powdered polymer product. The greatly improved clarity of the polymer gives it pronounced advantages over the native xanthan gum as well as other derivatives produced by prior art.

The heteropolysaccharides which are modified in accordance with the invention by reacting them with alkaline agents are heteroglycans produced by the action of bacteria of the genus Xanthomonas upon carbohydrates. Representative species of these bacteria include *Xanthomonas begoniae*, *Xanthomonas campestris*, *Xanthomonas carotae*, *Xanthomonas hedrae*, *Xanthomonas incanae*, *Xanthomonas malvacearum*, *Xanthomonas papavericola*, *Xanthomonas phaseoli*, *Xanthomonas pisi* and *Xanthomonas translucens*. Laboratory work has indicated that production of the heteropolysaccharides is a characteristic trait of all members of the genus Xanthomonas. Experiments have shown that certain species of these bacteria produce the polymers with particular efficiency and are therefore more attractive for purposes of the invention than are others. *Xanthomonas begoniae*, *Xanthomonas campestris*, *Xanthomonas incanae* and *Xanthomonas pisi* are particularly outstanding in this respect and are therefore preferred for purposes of the invention.

Organisms of the Xanthomonas genus act upon a wide variety of carbohydrates to produce the heteropolysaccharides utilized for purposes of this invention. Suitable carbohydrates include glucose, soluble starch, corn starch and the like. Fermentation studies have shown that the carbohydrates employed need not be in a refined state and may instead be utilized in the form of crude materials derived from natural sources. Specific examples of such crude materials include raw sugar, crude molasses, sugar beet juice, raw potato starch and the like. Since the crude materials are generally much less expensive than the corresponding refined carbohydrates, they are, in most cases, preferred for use as substrates in preparing the heteropolysaccharides.

The heteropolysaccharides are normally produced from carbohydrates such as those described above by employing an aqueous fermentation medium from about one to about 5 weight percent of the carbohydrate. From about 0.1 to about 0.5 weight percent of dipotassium acid phosphate and from about 0.1 to about 10 weight percent of a nutrient containing suitable trace elements and organic nitrogen sources is usually added to the carbohydrate solution to complete the fermentation medium. The nutrient employed will normally be a byproduct material such as distillers' solubles or the like. A mixture containing 2 weight percent raw sugar, 0.4 weight distillers' solubles has been found to yield excellent results. The use of such a mixture is not necessary in all instances however. The trace elements and organic nitrogen sources contained in the nutrient are apparently also present in certain of the crude carbohydrate source materials: raw sugar beet juice, for example, and hence, it has been found that the addition of a nutrient to such materials may not be necessary.

Fermentation of the medium thus prepared to produce the heteropolysaccharides is carried out by first sterilizing the medium and then inoculating it with bacteria of the genus Xanthomonas. The fermentation reaction is conducted under aerobic conditions and hence, sterilized air is bubbled through the medium as it ferments. The medium is maintained at a temperature between about 70°F. and about 100°F., preferably between about 75°F. and about 85°F., for a period from about 1 to about 3 days. As the fermentation reaction progresses, the viscosity of the medium increases rapidly due to formation of the heteropolysaccharide. The rate of fermentation is controlled to some extent by the pH of the fermenting medium. In general, fermentation takes place most rapidly at pH values between about 6.0 and about 7.5. Control of the pH at a level between about 6.5 and about 7.2 is preferred. Sodium hydroxide or a similar alkaline material may be added to the medium continuously or at intervals in amounts sufficient to maintain the pH levels within the desired time range. After the viscosity of the medium has reached a value of about 70 centipoises or higher, as determined by testing the fermentate in 1:6 dilution with distilled water with a Brookfield viscometer at 80°F., the reaction may be halted. In a well controlled fermentation process, this point is normally reached after about 48 hours. The crude heteropolysaccharide produced by fermentation can then be separated from the bacterial cells by centrifugation or filtration, if desired. Precipitation with methanol, ethanol, acetone or a similar reagent permits isolation of the relatively pure heteropolysaccharide. Separation of the heteropolysaccharide from the bacterial cells and subsequent precipitation is not essential in preparation of the improved thickening agent of the invention, however, and thus, these steps may be omitted in order to reduce the cost of preparing the thickening agent.

The heteropolysaccharide prepared by the action of bacteria of the genus Xanthomonas on carbohydrates is normally obtained as a thick viscous solution having a dull yellow color. Analytical work has shown that the heteropolysaccharide itself is a heteroglycan containing mannose, glucose, glucuronic acid salts and acetyl groups on a molar ratio of about 2:1:1:1, respectively. Also present may be about 5.5 weight percent of inorganic materials plus about 0.15 weight percent of each phosphorous and nitrogen. The above ratios and percentages may vary slightly in some cases, depending on the particular Xanthomonas species and the carbohydrates employed in the fermentation reaction. Studies have shown, however, that the materials produced by the various organisms from a wide variety of substrates are identical, for all practical purposes. When dried, the relatively pure heteropolysaccharides are soft, bulky powders, slightly tinted by colored materials from the culture medium. They swell rapidly in the presence of small amounts of water and are readily soluble in larger quantities of water.

Xanthan gums, heteropolysaccharides which may be obtained in the manner set forth in the preceeding paragraphs, are converted into the improved thickening agents of the invention by reacting them with an excess of base under controlled conditions. Preferred bases include those compounds which, when dissolved in water, produce only monovalent cations, for example, sodium, potassium and ammonium. Of these, sodium is preferred because of its low cost and ready availability. Reaction of xanthan gum and the base is carried out by adjusting the pH of an aqueous solution containing the gum to above 8.0, preferably 11.8 – 12.8. It has been observed that polyvalent cations will cause the polymer to precipitate at a pH in excess of about 11.5. For this reason, the use of a base such as calcium hydroxide is not generally suitable.

It is normally preferred to employ the crude polysaccharide solution produced in the fermentation step for this purpose, but an aqueous solution containing the purified xanthan gum in a concentration between 0.1 and 3%, by weight, may be utilized, if desired. In instances where a purified xanthan gum is utilized, it is satisfactory to adjust the pH of the solution to the desired level or slightly above before dissolving the gum. The reaction mixture is heated to a temperature in excess of about 100°F., preferably between 150°F. and 250°F. The solution is held at this temperature for a period from about one minute to 100 minutes or more, after which it is cooled. It has been found that elevated temperatures greatly accelerate the reaction rate. The pH of the solution may then be adjusted to the range of 4 to 9, preferably about pH 7, with any suitable acid. Hydrochloric acid is preferred due to the high solubility of chloride salts, however, for the preparation of a food additive, an organic salt, such as acetic acid, may have certain advantages.

Although contact of xanthan gum with a base under the conditions described produces little change in the viscosity characteristics of the polymer solution, analysis by both infrared and ultraviolet absorption has shown that the product is substantially different from the original xanthan gum.

The modified heteropolysaccharide solution produced in the manner set forth above may be stored in liquid form for subsequent use as a thickening agent or may, instead, be dehydrated and packaged in dry form for future use or shipment. It is normally preferred to dehydrate the solution in a spray dryer or similar equipment to reduce the expense of shipping the finished product.

Further objects and attendant advantages of the invention will be apparent by the reference to the following description of the polymer recovery process and to FIG. I, the attached drawing illustrating that process.

The apparatus shown includes a tank 14 in which the pH of the fermented beer, or other aqueous medium containing polymer, made by bacteria of the genus Xanthomonas, is adjusted to about 12.0 by the addition of any suitable alkaline reagent through line 13. Preferred alkaline reagents contain a minimum quantity of polyvalent cations. Sodium, potassium and ammonium hydroxide are useful reagents with sodium hydroxide generally preferred because of its low cost, availability and temperature stability. High pH alone is sufficient to promote the desired clarification reactions, however, the reaction proceeds much faster at elevated temperatures. To accelerate the process, steam is sparged through line 15 to raise the temperature to between 80°F. and 250°F., preferably about 200°F. If dilution of the reaction mixture is objectionable, a jacket or heating coil may be employed.

The progress of the reaction is conveniently followed by using a spectrophotometer to precisely measure the clarity of the reaction mixture. If the spectrophotometer is adjusted to give zero transmittance at time zero, during the course of the reaction, the transmittance readings will increase to above about 70%. The final clarity will be approached slowly and therefore, the reaction can be stopped after it has proceeded to any degree desired. The long times required to achieve the full degree of clarity often make it advantageous to stop the reaction short of completion.

If it is desired to harvest the polymer product by precipitation with alcohol, the solution in tank 14, after achieving the desired clarity, is pumped through mixing line 21, where it is blended with the stream containing isopropyl alcohol, which enters at mixing tee 22. Precipitation is effected and the slurry proceeds to a screen, 24, where it is filtered from the free liquid phase. Studies have shown that the precipitate contains 80% to 95% bound liquid which can not be removed by filtration. The wet, gelatinous precipitate feeds from the filter to squeeze rolls, 26, which reduce the liquid content of the precipitate to about 75%.

The pressed cake is then fed, as indicated by line 27, to the dryer, 28, and is then passed through line 29 to mill 30, where it is pulverized. The finely ground dried product, which readily hydrates in water producing a viscous dispersion having greatly improved clarity as compared to the native xanthan gum, is withdrawn from the mill as indicated by line 31.

It will be understood that the foregoing description and FIG. I of the drawing are directed to a specific process for preparing the improved thickening agent of the invention and that the invention itself is not limited to the precise reactants and apparatus described. The process depicted in the drawing is essentially a batch type operation. Such a process can obviously be converted into a continuous operation by continuously introducing fresh reactants and withdawing the product from the reactor vessel and by making other minor modifications. It will be recognized that instrumentation, steam lines and other features conventional in processes such as that described above have not been set forth in detail. These and similar features will be familiar to those skilled in the art and need not be specifically set forth in order to permit full understanding of the invention.

The process of the invention can be further illustrated by referring to the results obtained in a series of experiments wherein the modified heteropolysaccharide was prepared in accordance with the invention and was tested to determine effectiveness for thickening aqueous media.

In preparation for the comparison experiments, 4 grams of a commercially available xanthan gum, Kelzan XC, were dissolved in 400 cc of an aqueous solution of sodium hydroxide. Prior to dissolution of the gum, the pH of the solution was 12.8. The reaction mixture was placed in a hot water bath at 75°C. for three hours. After about two hours, the sample started to clarify and at the end of 3 hours, it had the appearance of a true solution. The reaction mixture was neutralized by adding a small amount of 5N hydrochloric acid and then cooled to room temperature for testing. A control solution of xanthan gum was prepared in a like manner by dissolving 4 grams of Kelzan XC in 400 cc of distilled water, (pH 7.2), followed by heating to 75°C. for three hours.

Samples of xanthan gum treated with sodium hydroxide as described above and the control xanthan gum were analyzed by means of an infrared spectrometer. The absorption curves for the two samples contain peaks as shown in the following Table:

Table I

| INFRARED ABSORPTION PEAKS | | |
|---|---|---|
| Control Heteropolysaccharide Kelzan XC | Modified Heteropolysaccharide Produced by Reaction with NaOH | Heteropolysaccharide Substituted by Reaction with Formaldehyde |
| Microns | Microns | Microns |
| 3.0 | 3.0 | 3.0 |
| 3.4 | 3.4 | 3.4 |
| — | 4.3 | — |
| 5.8 | — | 5.8 |
| 6.2 | 6.2 | 6.2 |
| 7.1 | 7.1 | 7.1 |
| 7.3 | 7.3 | 7.3 |
| 8.1 | 8.1 | 8.1 |
| 8.6–10.2 | 8.6–10.2 | 8.6–10.2 |
| — | 10.8 | 10.8 |
| 11.3 | 11.3 | — |
| 12.4 | 12.4 | 12.3–12.8 |
| 12.9 | 12.9 | — |
| — | 15.2 | — |

Table I-continued

| INFRARED ABSORPTION PEAKS | | |
|---|---|---|
| Control Heteropoly-saccharide Kelzan XC | Modified Heteropolysaccharide Produced by Reaction with NaOH | Heteropolysaccharide Substituted by Reaction with Formaldehyde |
| 15.6 | 15.6 | — |

The above table clearly demonstrates that the chemical structure of xanthan gum treated with sodium hydroxide, a modified heteropolysaccharide, differed from that of the native xanthan gum control, Kelzan XC. The predominant peaks shown by the modified heteropolysaccharide at 4.3, 10.8 and 15.2 microns and the absence of a peak at 5.8 microns clearly indicate that the reaction product possesses a characteristic chemical structure which is unique and differentiates it from the unreacted heteropolysaccharide, xanthan gum, used as the control. Data on absorption spectra for xanthan gum which has been reacted with formaldehyde, as taught in U.S. Pat. No. 3,020,207, are shown in Column III of the above table. The prominent peaks at 4.3 and 15.2 microns are missing in the spectra of the aldehyde product and in addition, the aldehyde product shows a definite peak at 5.8 microns, which is not present in the spectra of the modified heteropolysaccharide of this invention. These differences in spectra further illustrate the unique chemical structure of the modified heteropolysaccharide. It is thus apparent that treatment of xanthan gums with alkaline agents produce a new composition of matter having properties unlike those of the native xanthan gums or substituted heteropolysaccharides heretofore described by the prior art.

To compare the rheological properties of the modified heteropolysaccharide with the control polymer, portions of each solution were diluted to obtain a polymer concentration of one pound per barrel. This is equivalent to 1 gram of polymer per 350 cc of liquid. 0.2 Grams of chromic chloride was added to 350 cc samples of both the modified polymer and the control. The pH of both solutions was increased to 8.5 by the addition of 2.0N sodium hydroxide solution. Viscosity measurements were made at 75°F. with a Fann viscometer. The results obtained are shown in Table II.

Table II

| RHEOLOGY OF THICKENING AGENTS CROSS-LINKED WITH CHROMIC CHLORIDE | | | | |
|---|---|---|---|---|
| Agent | Apparent Viscosity | Plastic Viscosity | Yield Point | Ratio YP/PV |
| Control Xanthan gum | 16 | 8 | 16 | 2.0 |
| Modified Heteropolysaccharide | 21 | 9 | 24 | 2.7 |

From the above table, it can be seen that the modified heteropolysaccharide is more viscoelastic than the control polymer. The large increase in yield point is indicative of the elastic properties of the solution and the increased ratio of yield point to viscosity is indicative of improved shear thinning and cuttings carrying properties of the modified polymer. Both of these properties are highly desirable in a polymer used in oil well drilling fluids. It also suggests the use of the modified polymer in water-base paints to reduce drag on the brush and the tendency to drip.

To quantify the obvious improved clarity of the solutions prepared with the modified polymer, samples of the test and control solutions described above were diluted with simulated sea water to obtain solutions having polymer concentrations varying from 200 to 1000 parts per million. Light absorption measurements were made using a Spectronic 20 and a wave length of 700 millimicrons. The results of these measurements are shown in Table III.

Table III

CLARITY OF THICKENED LIQUIDS

Light Absorption λ = 700 millimicrons

| Agent | pH | Polymer Concentration, ppm | | |
|---|---|---|---|---|
| | | 1000 | 500 | 200 |
| Control Xanthan gum at 1000 ppm | 11.7 | .55 | .30 | .14 |
| Modified Heteropolysaccharide | 11.7 | .09 | .05 | .03 |
| Modified Heteropolysaccharide chloride | 5.0 | .18 | .06 | .03 |

From the above table, it can be seen that the modified heteropolysaccharide produced solutions which were significantly clearer than those of the control. The improved clarity was obtained in the presence of high concentrations of salt, indicating the usefulness of the modified polymer for preparing clear, viscous liquids over a wide range of salinities and pH's. This property is desirable in a polymer used to thicken foodstuffs, such as clear puddings, barbecue sauces, to stabilize beer foam, and is also desirable for polymer solutions used in the petroleum field for waterflooding, drilling and completion operations.

The superiority of the solutions prepared with the modified polymer in terms of flowability through petroleum reservoirs can be seen by comparing the results obtained in flow tests where solutions were passed through cores cut from a subsurface formation. The core used for the tests was Berea sandstone and had an initial permeability to water in the presence of residual oil of 32.6 millidarcys. Portions of the modified heteropolysaccharide and the control, Kelzan XC, previously described, were diluted with simulated sea water to a polymer concentration of 500 parts per million. The modified polymer solution was crystal clear while the control was cloudy and opaque. These solutions were injected into a test specimen and the results obtained are shown in Table IV.

Table IV

FLOWABILITY OF VISCOUS BRINE IN RESERVOIR CORES

| Pore Volumes Viscous Brine Injected | Core Permeability, per cent of Original Permeability | |
|---|---|---|
| | Control Xanthan Gum | Modified Heteropolysaccharide |
| 0.00 | 100 | 100 |

Table IV-continued
FLOWABILITY OF VISCOUS BRINE IN RESERVOIR CORES

| Pore Volumes Viscous Brine Injected | Core Permeability, per cent of Original Permeability | |
|---|---|---|
| | Control Xanthan Gum | Modified Heteropolysaccharide |
| .31 | 5 | 100 |
| .38 | 4 | 100 |
| .68 | 3 | 96 |
| 1.15 | ~0 | 94 |
| 2.96 | — | 88 |
| 3.46 | — | 83 |
| 4.23 | — | 81 |
| 5.00 | — | 82 |

The above data illustrates the remarkable improvement in flowability which resulted from the reaction of xanthan gum with sodium hydroxide. It can be seen that the control solution effectively plugged the core before even one pore volume could be injected. In contrast, the solution containing the modified polymer was easily injected and caused an inconsequential, and in fact, desirable decrease in the permeability of the test specimen. It is thus clear that thickening agents of the invention are much better suited for use in waterflooding and similar operations than native xanthan gum and similar agents frequently advocated for use in such operations in the past.

What is claimed is:

1. A process for preparing an improved thickening agent which comprises dispersing a heteropolysaccharide produced by the action of bacteria of the genus Xanthomonas on a carbohydrate in an aqueous reaction medium substantially free of polyvalent cations, increasing the pH of said reaction medium by the addition of NaOH, KOH, or $NH_3$ to above about 11, heating said reaction medium to a temperature above 150°F and maintaining the medium at this elevated temperature for a period of time to effect clarification.

2. A process as defined in claim 1 wherein said alkaline compound is sodium hydroxide.

3. A process as defined claim 1 wherein the reaction medium is maintained at a temperature between 180° and 230°F for the period of time required to effect clarification.

4. A process as defined in claim 1 wherein said bacteria are of the species *Xanthomonas campestris*.

5. A process as defined in claim 1 wherein the resulting clarified reaction mixture is diluted and circulated in contact with a subsurface geologic formation.

6. A process as defined in claim 1 wherein the reaction medium is heated by direct contact with steam.

7. A process for synthesizing an improved thickening agent consisting of reacting at an elevated temperature between 150° and 250°F a heteropolysaccharide produced by bacteria of the genus Xanthomonas in an aqueous reaction medium substantially free of polyvalent cations and having a pH above about 11, said elevated pH being obtained by the addition of sodium hydroxide, potassium hydroxide or ammonia, and recovering said thickening agent, distinguishable from the original heteropolysaccharide by its IR spectra, from the reaction medium by precipitation with alcohol.

8. A process as described in claim 7 wherein precipitation is accomplished by the addition of isopropyl alcohol.

* * * * *